United States Patent [19]

Kilpatrick et al.

[11] Patent Number: 4,913,902

[45] Date of Patent: Apr. 3, 1990

[54] PURIFICATION BY AFFINITY BINDING TO LIPOSOMES

[75] Inventors: Peter K. Kilpatrick; Ruben G. Carbonell; Johnny D. Powers, all of Raleigh, N.C.

[73] Assignee: North Carolina State University, Raleigh, N.C.

[21] Appl. No.: 119,351

[22] Filed: Nov. 10, 1987

[51] Int. Cl.$^4$ .............................................. A61K 39/00
[52] U.S. Cl. ...................................... 424/85.8; 424/88; 424/450; 435/183; 530/412; 530/413; 536/27; 536/28; 436/829
[58] Field of Search ................. 530/413; 436/829; 424/450, 85.8, 88; 435/183; 536/27, 28

[56] References Cited

U.S. PATENT DOCUMENTS

| | | |
|---|---|---|
| 4,483,929 | 11/1984 | Szoka . |
| 4,522,803 | 6/1985 | Lenk et al. . |
| 4,529,561 | 7/1985 | Hunt et al. ............... 436/829 |
| 4,564,599 | 1/1986 | Janoff et al. . |
| 4,588,578 | 5/1986 | Fountain et al. . |
| 4,610,868 | 9/1986 | Fountain et al. . |
| 4,666,831 | 5/1987 | Janoff et al. . |
| 4,668,638 | 5/1987 | Janoff et al. . |
| 4,698,299 | 10/1987 | Janoff et al. . |
| 4,707,441 | 11/1987 | Ahmad et al. ............ 435/7 |
| 4,737,323 | 4/1988 | Martin et al. ............. 436/829 |
| 4,766,046 | 8/1988 | Abra et al. ............... 436/829 |
| 4,781,871 | 11/1988 | West et al. ............... 424/450 |
| 4,783,264 | 11/1988 | Nylen et al. ............. 210/638 |

FOREIGN PATENT DOCUMENTS 127737 12/1984 European Pat. Off. .

OTHER PUBLICATIONS

Brendzel et al–Chem. Abst. vol. 92 (1980) p. 123,732x.
Margolis et al–Chem. Abst. vol. 99 (1983) p. 209,031z.
Liautard et al–Chem. Abst. vol. 104 (1986) p. 105,499p.
Alving, Carl R. and Richards, Roberta L., *Immunochemistry* 14, 373 (1977).
Mattiasson, B. and Ramstorp, M., "Ultrafiltration Affinity Purification", Ann. N.Y. Acad. Sci. 413, 307 (1983).
Mattiasson, B. and Ling, T., Chapter 5 in Bioprocess Technology, 1 Membrane Separations in Biotechnology, W. C. McGregor, editor, Marcel Dekker, Inc., New York, 99 (1986).

*Primary Examiner*—Sam Rosen
*Attorney, Agent, or Firm*—Bell, Seltzer, Park & Gibson

[57] ABSTRACT

A method of extracting a compound specifically bound by a ligand from a crude solution containing the compound is disclosed. The method comprises providing a multiplicity of liposomes having the ligand bound to the surface thereof, and mixing the liposomes with the crude solution so that the ligand binds to the compound to be extracted. The liposomes are then separated from the crude solution and the compound to be extracted recovered from the liposomes.

20 Claims, No Drawings

# PURIFICATION BY AFFINITY BINDING TO LIPOSOMES

FIELD OF THE INVENTION

This invention relates to affinity purification generally, and particularly relates to an affinity purification procedure in which ligands are bound to liposomes.

BACKGROUND OF THE INVENTION

Bioactive macromolecules (e.g., enzymes, antigens, antibodies, and hormones) are typically produced in low concentration by normal or genetically-altered microbial fermentation broths. Undesired impurities in the broth may include large biomolecules, cell organelles, membrane lipids, amino acids, saccharolytic substrates, and a host of electrolytes. Among the industrial and labscale purification schemes which are presently used to purify bioactive macromolecules are crystallization, ion exchange chromatography, hydrophobic chromatography, electrophoresis, and affinity chromatography. See generally Bonnerjea, J. et al., Bio/Technology 4, 955 (1986). The latter technique, affinity chromatography, is by far the most selective technique but is very difficult to scale up, and the activation of the gel beads with affinity ligands is an expensive procedure that is difficult to control.

Recently, Mattiason and Ling employed particle-bound affinity ligands to specifically purify proteins from solution. See Bioprocess Technology, 99 (McGregor, W.C., ed. 1986) (Marcel Dekker, Inc., N.Y.); see also European patent application publication no. 0127737. Ligands were immobilized on starch granules or particulate heat-killed yeast cells, and subsequently mixed with the solution. After allowing affinity binding to occur, the impurities were removed by ultrafiltration through a membrane which retained the solid particles. The authors suggest that the technique can be scaled up for large-scale purification, but note that the maximum amount of macromolecules that can be bound is limited by the available surface area of the particles. In addition, the authors note that the fouling and clogging of membranes is a potential problem with this technology. Finally, the authors do not suggest any general scheme by which a variety of different ligands may be bound to the small particles they employ. Accordingly, an object of the present invention is to provide an affinity purification procedure employing small particles with large surface areas, which particles do not cause undue fouling of filters or semipermeable membranes, and which particles are convenient carriers for a variety of different ligands.

DESCRIPTION OF THE INVENTION

The foregoing objects are achieved by the method of extracting a compound specifically bound by a ligand from a crude solution containing the compound, as disclosed herein. The crude solution contains the compound to be extracted and at least one contaminating compound. The method comprises providing a multiplicity of liposomes, the liposomes having the ligand bound to the surface thereof. The liposomes are mixed with the crude solution so that the ligand binds to the compound to be extracted. The liposomes are then separated from the crude solution, and the compound to be extracted recovered from the liposomes.

The step of separating the liposomes from the crude solution may be carried out by passing the crude solution through a filter impermeable to the liposomes. The step of recovering the compound to be extracted from the liposomes may comprise the steps of suspending the liposomes in a solution, and mixing an additional quantity of the ligand, free from the liposomes, in the solution to facilitate dissociation of the compound to be extracted from the ligand bound to the liposome. However, any technique conventionally employed in affinity chromatography to remove compounds to be extracted from the ligand, such as pH change or change in ionic strength of the solution in which the liposomes are suspended, may also be employed.

Liposomes, also called lipid vesicles, are smooth and spherical and have been known for a number of years as convenient carriers of encapsulated water soluble materials. Several methods are available to make liposomes. See e.g., Bangham et al., J. Mol. Biol. 13, 238 (1965); D. Papahadjopoulos and N. Miller, Biochim. Biophys. Acta 135, 624 (1967); Deamer and Bangham, Biochim. Biophys. Acta 443, 629 (1976); Papahadjopoulos et al., Biochim. Biophys. Acta 394, 483 (1975); German Patent No. 2,532,317; and U.S. Pat. Nos. 3,804,776; 4,016,100; 4,235,971; 4,522,803; and 4,588,578. The disclosure of all U.S. patent references cited herein are incorporated herein by reference.

Liposome wall forming compounds are generally well known, as are the methods of their preparation. For example, any number of phospholipids or lipid compounds may be used to form the vesicle walls. Representative of such wall forming compounds are those described in U.S. Pat. No. 4,235,871. Specific examples of suitable lipids useful in the production of liposomes are phospholipids, which include, but are not limited to, the natural lecithins or phosphatidylcholines (e.g., egg lecithin or soybean lecithin) and synthetic lecithins, such as saturated synthetic lecithins (e.g., dimyristoylphosphatidylcholine, dipalmitoylphosphatidylcholine and distearoylphosphatidylcholine) and unsaturated synthetic lecithins (e.g., dioleoylphosphatidylcholine and dilinoleoylphosphatidylcholine). Other phospholipids include, but are not limited to, phosphatidylethonolamine, lysolecithin, lysophosphatidylethanolamine, phosphatidylserine, phosphatidylinositol, sphingomyelin, cardiolipin, phosphatidic acid, ceramides and cerebrosides. The liposome wall can optionally contain a steroid component such as cholesterol, coprostanol, cholestanol, cholestane and the like. The liposome wall may optionally be polymerized to increase its stability. See generally Tundo et al., J. Am. Chem. Soc. 104, 456 (1982); Regen et al., J. Am. Chem. Soc. 104, 791 (1982).

To achieve the greatest benefit from the large surface areas which liposomes provide, the liposomes used in the present invention preferably have diameters of about 500 nanometers or less. More preferably, the liposomes have diameters of from 20 to 100 nanometers, and most preferably the liposomes have diameters of from 20 to 50 nanometers. Some larger diameter liposomes may optionally be included with small liposomes of the desired size range, but it is the small liposomes which advantageously provide increased surface areas for ligand binding. Small unilamellar vesicles are particularly preferred for practicing the present invention because of their high surface areas and their stability over time.

Filters used to separate liposomes from crude solutions may be commercially available ultrafiltration and microfiltration membranes. The only restriction on the membrane used is that the pore size of the membrane be smaller than the diameter of the liposomes. Membranes having pore diameters of about 250 nanometers or less are preferred, membranes having pore diameters of from about 3 nanometers to about 50 nanometers are more preferred, and membranes having pore diameters of from about 3 nanometers to about 25 nanometers are most preferred.

Ligands which will bind to any of a variety of target molecules can be bound to liposomes to practice the present invention. Exemplary of such ligands, and the target molecules bound thereby, are the following: Biotin and Avidin; Monoclonal Antibodies and Inhibin; Procainamide and Cholinesterase; N-methyl Acridinium and Acetylcholinesterase; P-aminobenzamidine and Trysin; P-aminophenol-beta-D-thiogalacto-pyranoside and Beta-Galactosidase; Chitin and Lysozyme; Methotrexate and Dihydrofolate Reductase; AND and Alcohol Dehydrogenase; Sulfanilamide and Carbonic Anhydrase; DNA and DNA Polymerase; DNA and cDNA; DNA and RNA; cDNA and Genetically Engineered Plasmids; Oxidized Glutathione and Glutathione Reductase; P-aminobenzamidine and Urokinase; Monoclonal Antibodies and Insulin; Trypsin and Soybean Trypsin Inhibitor; $N^6$-aminocaproyl-3',5'-cAMP and Protein Kinase; Pepstatin and Renin; 4-Chlorobenzylamine and Thrombin; Monoclonal Antibodies and Interferon; N-(4-amino phenyl) Oxamic Acid and Influenza Virus; Prealbumin and Retinal-binding Protein; Neurophysin and Vasopressin; Lysine and Plasminogen; Heparin and Antithrombin; Cycloheptaamylose and Human Serum Amylase; Cortisol and Transcortin; Pyridoxal-5-phosphate and Glutamate-pyruvate transaminase; Chelating Agents and Metal Ions; Chelating Agent-Cu and Superoxide Dismutase; Chelating Agent-Zn and Human Fibrinogen; Coenzyme A and Succinic Thiokinase; Flavin and Luciferase; Pyridoxal Phosphate and Tyrosine Aminotransferase; Porphyrin and Haemopexin; Lysine and Ribosomal RNA; Polyuridine and mRNA; Concanavalin A and Immunoglobulins; 3-phospho-3hydroxypropionate and Enolase; D-malate and Fumarate Hydratase; Atropine or Cobratoxin and Cholinergic Receptors; 6-Aminopenicillanic acid and D-Alanine Carboxypeptidase; Plant Lectins and Epidermal Growth Factor Receptors; Alprenolol and Epinephrine Receptors; Growth Hormone and Prolactin Receptors; Insulin and Insulin Receptors; Estradiol or Diethylstilbestrol and Estrogen Receptors; Dexamethasone and Glucocorticoid Receptors; Hydroxycholecalciferol and Vitamin D Receptors; Virus Monoclonal Antibodies and Blood Viruses; and Monoclonal Antibodies and Bacteriophages. Suitable chelating agents for practicing the present invention include ethylenediaminetetraacetic acid (EDTA) and other compounds containing the iminodiacetic acid group, phosphonoacetic acid ($H_2O_3P-CH_2COOH$), pyrophosphate (such as dibasic pyrophosphate hexahydrate), dibasic orthophosphate, crown ethers such as dicyclohexano-18-crown-6, cyclodextrins, cryptands. In overview, suitable ligands include, but are not limited to, antibodies, peptides, polynucleic acids, antitoxins, chelating agents, enzyme inhibitors, receptor agonists, and receptor antagonists. The term "antibody," as used herein, means immunoglobulins such as IgA, IgG, IgM, IgD, and IgE, whether polyclonal or monoclonal in origin. These ligands may be covalently bound to phospholipids used to form liposomes by conventional techniques, either by attaching the ligand to preformed liposomes or by binding the ligand to a phospholipid and incorporating the resulting amphiphilic molecules into liposomes during formation thereof. For example, liposomes with antibodies linked thereto may be produced in the manner disclosed in U.S. Pat. No. 4,483,929 to Szoka.

The present invention will be explained in further detail in the following nonlimiting examples. These examples are for illustrative purposes only, and are not to be taken as restricting the scope of this invention.

EXAMPLE 1

Preparation of Biotinylated Phospholipid

Biotin was coupled to dimyristoyl phosphatidylethanolamine (DMPE) according to the procedure of Bayer et al., *Biochim. Biophys. Acta* 550, 464 (1979). DMPE (48 micromoles) was dissolved in a 1 ml solution of chloroform/methanol (volume ratio 2:1) containing 60 micromoles of biotinyl-N-hydroxysuccinimide ester (BNHS). Triethylamine (10 microliters) was added to act as a proton-accepting catalyst and the mixture was allowed to react at room temperature for 30 minutes. The biotinylated DMPE was separated from unreacted BNHS by preparative thin-layer chromatography on 1mm thick silica gel plates, using chloroform/methanol/water (volume ratio 80:25:2) as the developing solvent system. The biotinylated phospholipid was identified by both a biotin-specific spray reagent, McCormick, D. and Roth, J., *Meth. Enzymol.* 18, 383 (1970) (dimethylaminocinnamaldehyde, 0.2% in acidified ethanol) and a phosphate-specific spray. Dittmer, J. and Lester, R.C., *J. Lipid Res.* 5, 126 (1964) (molybdenum blue reagent). The product was scraped off the plate and extracted with chloroform/methanol (volume ratio 2:1). The solvent was evaporated at 40° C. in a rotary evaporatrr and the dry product was weighed to determine the yield. Typically, 75% of the theoretical yield was obtained. The DMPE-biotin was stored under nitrogen at −4° C.

EXAMPLE 2

Preparation of Liposomes

To prepare the lipid dispersion, dimyristoyl phosphatidylcholine (74 micromoles) and biotinylated DMPE (4 micromoles) were dissolved in 20 ml of chloroform/methanol (volume ratio 2:1). After thorough mixing, the solution was dried in a rotary evaporator at 40° C. for 1 hour and the dried phospholipids were suspended in buffer (0.1M NaCl, 0.01M tris-HCl, pH 8.5) at a concentration of 5 weight %. The dispersion was sonicated for 8 hours at 33° C. in a Heat Systems Ultrasonic Sonicator (model W-385) equipped with a cup horn. Sonication for eight hours converted large unilamellar vesicles to small unilamellar vesicles ranging from about 20 to about 100 nanometers in diameter. Undispersed phospholipid was removed by centrifugation at 8000 g for 20 minutes and the remaining vesicles were fractionated by size exclusion chromatography on a Sepharose CL-4B-200 column (2×30 cm). See Huang, C., *Biochemistry* 8, 344 (1969). The absorption of the column effluent at 300 nm was continuously monitored by a Bausch and Lomb Spectronic 21 spectrophotometer equipped with a flow cell. The effluent was collected in a Gilson model 203 fraction collector, and the fractions were concentrated by ultrafiltration through an Amicon ultrafiltration unit (model 8200) with a 100,000 molecular weight cutoff membrane (Amicon YM100). The liposomes were kept at 35° C in a constant temperature water bath and were used within five days.

EXAMPLE 3

Avidin Purification and Recovery

Small unilamellar liposomes prepared as described in Example 2 above (12.5 mg/ml) were added to a mixture of avidin and lysozyme to demonstrate that avidin can be specifically separated and recovered from a heterogeneous solution. 200 microliters of the biotinylated liposomes were added to a 10 ml solution of 0.06 mg/ml avidin and 0.5 mg/ml lysozyme. HPLC analysis showed that after four hours, 73 percent of the avidin was bound, while all of the free lysozyme was still present in solution. The solution was then diluted with 10 ml ammonium carbonate buffer and ultrafiltered though an Amicon YM100 membrane to remove the lysozyme and remaining unbound avidin. The flux through the membrane remained essentially constant throughout the ultrafiltration (0.14 ml water/cm$^2$ min) using an upstream pressure of 40 psig. This indicates that the liposomes do not appreciably foul the membrane. HPLC analysis of the filtrate and retentate revealed that all of the lysozyme and free avidin was in the filtrate. To recover the avidin from the liposomes, a 100-fold molar excess of free biotin was added to the solution. The solution was allowed to stand overnight and then filtered through a 10,000 molecular weight cutoff membrane (YM10) to remove the unbound biotin. The concentrate was filtered through a YM100 membrane to separate the free avidin-biotin complexes from the liposomes. The filtrate contained 20 percent of the avidin that was originally bound to the liposomes. This solution was then ultrafiltered (YM100) down to less than 1 ml, and 10 ml of 6N guanidine-HCl (pH 1.5) was added to remove the biotin. After five minutes, this solution was reconstituted in ammonium carbonate buffer, which rendered the avidin 76 percent active. This experiment was repeated using a larger biotin excess (1000-fold molar excess). This time, approximately 50 percent of the liposime-bound avidin was recovered.

The invention described above may be used for a broad variety of separation procedures, and practiced with a variety of different types of apparatus, including both batch and continuous flow apparatus. Accordingly, the foregoing discussion is to be considered illustrative, and not limiting, with the scope of the present invention being defined by the following claims. Equivalents of the claims are to be included therein.

That which is claimed is:

1. A method of purifying a compound specifically bound by a ligand from a crude solution containing that compound and other compounds, the method comprising:
   (a) providing a multiplicity of liposomes, the liposomes having said ligand bound to the surface thereof;
   (b) mixing the liposomes having said ligand bound to the surface thereof with the crude solution so that the ligand binds to the compound to be extracted;
   (c) separating the liposomes from the crude solution by passing the crude solution including said other compounds through a filter, said filter having pores smaller in size than the diameter of said liposomes to restrain said liposomes from passing therethrough; and
   (d) separating and recovering the compound to be extracted from the liposomes which have been restrained from passing through the filter.

2. A method according to claim 1 wherein said step of recovering the compound to be purified from the liposomes comprises the steps of
   (a) suspending the liposomes in a solution; and
   (b) mixing an additional quantity of said ligand free from the liposomes in the solution to facilitate dissociation of the compound to be extracted from the ligand bound to the liposomes.

3. A method according to claim 1, wherein said liposomes have diameters of from 20 to 100 nanometers.

4. A method according to claim 1, wherein said ligand is an antibody.

5. A method according to claim 1, wherein said ligand is a polynucleic acid.

6. A method according to claim 1, wherein said ligand is a peptide.

7. A method according to claim 1, wherein said ligand is an antitoxin.

8. A method according to claim 1, wherein said ligand is a chelating agent.

9. A method according to claim 1, wherein said ligand is an enzyme inhibitor.

10. A method according to claim 1, wherein said ligand is selected from the class consisting of receptor agonists and receptor antagonists.

11. A method of purifying a compound specifically bound by a ligand from a crude solution containing that compound and other compounds, the method comprising:
    (a) providing a multiplicity of liposomes having diameters of about 500 nanometers or less, the liposomes having said ligand bound to the surface thereof;
    (b) mixing the liposomes having said ligand bound to the surface thereof with the crude solution so that the ligand binds to the compound to be extracted;
    (c) passing the crude solution including said other compounds through a filter impermeable to the liposomes to separate the liposomes from the crude solution; and
    (d) separating and recovering the compound to be extracted from the liposomes which have been restrained from passing through the filter.

12. A method according to claim 11, wherein said liposomes are formed from phospholipids, and wherein said ligands are covalently bound to said phospholipids.

13. A method according to claim 12, wherein said liposomes have diameters of from 20 to 100 nanometers.

14. A method according to claim 13, wherein said ligand is an antibody.

15. A method according to claim 13, wherein said ligand is a polynucleic acid.

16. A method according to claim 13, wherein said ligand is a peptide.

17. A method according to claim 13, wherein said ligand is an antitoxin.

18. A method according to claim 13, wherein said ligand is a chelating agent.

19. A method according to claim 13, wherein said ligand is an enzyme inhibitor.

20. A method according to claim 13, wherein said ligand is selected from the class consisting of receptor agonists and receptor antagonists.

* * * * *